United States Patent
Chen et al.

(10) Patent No.: US 10,159,700 B2
(45) Date of Patent: Dec. 25, 2018

(54) **METHOD OF TREATING *CLOSTRIDIUM DIFFICILE* INFECTION**

(71) Applicant: GENMONT BIOTECH INC., Tainan (TW)

(72) Inventors: Yi-Hsing Chen, Tainan (TW); Wan-Hua Tsai, Tainan (TW)

(73) Assignee: GENMONT BIOTECH INC., Tainan (TW)

( * ) Notice: Subject to any disclaimer, the term of this patent is extended or adjusted under 35 U.S.C. 154(b) by 0 days.

(21) Appl. No.: 15/366,193

(22) Filed: Dec. 1, 2016

(65) Prior Publication Data

US 2018/0050072 A1 Feb. 22, 2018

(30) Foreign Application Priority Data

Aug. 22, 2016 (TW) .............................. 105126799 A

(51) Int. Cl.
| | | |
|---|---|---|
| *A61K 35/747* | (2015.01) | |
| *C12R 1/225* | (2006.01) | |
| *C12N 1/20* | (2006.01) | |
| *A23L 33/135* | (2016.01) | |
| *A61K 35/00* | (2006.01) | |

(52) U.S. Cl.
CPC .......... *A61K 35/747* (2013.01); *A23L 33/135* (2016.08); *C12N 1/20* (2013.01); *C12R 1/225* (2013.01); *A61K 2035/115* (2013.01)

(58) Field of Classification Search
CPC ..................................................... C12R 1/225
See application file for complete search history.

(56) References Cited

U.S. PATENT DOCUMENTS

| 8,853,269 B2 | 10/2014 | Mosbaugh et al. |
| 2004/0057943 A1* | 3/2004 | Xaus Pey ............ A23C 9/1232 424/93.45 |
| 2006/0067921 A1 | 3/2006 | Conway |

OTHER PUBLICATIONS

Perez-Cano, Francisco J. ; Dong, Honglin; Yaqoob, Parveen. In vitro immunomodulatory activity of Lactobacillus fermentum CECT5716 and Lactobacillus salivarius CECT5713: two probiotic strains isolated from human breast milk. Immunobiology, 2010, 215. 12: 996-1004

Lin et al., "Antimicrobial Susceptibilities and Molecular Epidemiology of Clinical Isolates of Clostridium difficile in Taiwan", Antimicrobial Agents and Chemotherapy, Apr. 2011, vol. 55, No. 4, p. 1701-1705.

Zheng et al., "Complete Genome Sequence of emm1 *Streptococcus pyogenes* A20, a Strain with an Intact Two-Component System, CovRS, Isolated from a Patient with Necrotizing Fasciitis", Genome Announcements, Jan./Feb. 2013, vol. 1, Iss. 1, 2 pages.

Shih et al., "In Vitro and In Vivo Therapeutics of β-Thujaplicin on LPS-Induced Inflammation in Macrophages and Septic Shock in Mice", 2012, International Journal of Immunopathology and Pharmacology, vol. 25, No. 1, pp. 39-48.

* cited by examiner

*Primary Examiner* — Allison M Fox

(74) *Attorney, Agent, or Firm* — Muncy, Geissler, Olds & Lowe, P.C.

(57) ABSTRACT

A composition of *Lactobacillus fermentum* GMNL-296 and a use of *Lactobacillus fermentum* GMNL-296 for producing a composition to improve the infection symptoms of *Clostridium difficile* are provided. The *Lactobacillus fermentum* GMNL-296 is to promote the expression of anti-inflammatory cytokine IL-10 and Treg cell related transcription factors, so that the infection symptoms of weight loss and intestinal abnormalities are improved.

6 Claims, 4 Drawing Sheets

Specification includes a Sequence Listing.

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: PAF primer

<400> SEQUENCE: 1
agagtttgat cctggctcag                                              20
```

```
<210> SEQ ID NO 2
<211> LENGTH: 18
<212> TYPE: DNA
<213> ORGANISM: Artificial Sequence
<220> FEATURE:
<223> OTHER INFORMATION: 536R primer

<400> SEQUENCE: 2
gtattaccgc ggctgctg                                                   18

<210> SEQ ID NO 3
<211> LENGTH: 516
<212> TYPE: DNA
<213> ORGANISM: Artificial Sequence
<220> FEATURE:
<223> OTHER INFORMATION: Sequencing Primer

<400> SEQUENCE: 3
gggatacatg caagtcgaac gcgttggccc aattgattga tggtgcttgc acctgattga     60
ttttggtcgc caacgagtgg cggacgggtg agtaacacgt aggtaacctg cccagaagcg    120
ggggacaaca tttggaaaca gatgctaata ccgcataaca acgttgttcg catgaacaac    180
gcttaaaaga tggcttctcg ctatcacttc tggatggacc tgcggtgcat tagcttgttg    240
gtggggtaac ggcctaccaa ggcgatgatg catagccgag ttgagagact gatcggccac    300
aatgggactg agacacggcc catactccta cgggaggcag cagtagggaa tcttccacaa    360
tgggcgcaag cctgatggag caacaccgcg tgagtgaaga agggtttcgg ctcgtaaagc    420
tctgttgtta aagaagaaca cgtatgagag taactgttca tacgttgacg gtatttaacc    480
agaaagtcac ggctaactac gtgccagcag ccgggg                              516
```

METHOD OF TREATING *CLOSTRIDIUM DIFFICILE* INFECTION

CROSS REFERENCE TO RELATED APPLICATIONS

This application claims the benefit of the filing date of Taiwan patent application No. 105126799, filed on Aug. 22, 2016, the disclosure of which is incorporated herein by reference.

FIELD OF THE INVENTION

The present invention relates to a composition including *Lactobacillus Fermentum* GMNL-296 and a use of the *Lactobacillus Fermentum* GMNL-296 to produce the composition for improving infection symptoms of *Clostridium Difficile*, and in particular relates to a composition including *Lactobacillus Fermentum* GMNL-296 and a use of the *Lactobacillus Fermentum* GMNL-296 to produce the composition for treating or preventing from infection symptoms of *Clostridium Difficile*.

BACKGROUND OF THE INVENTION

*Clostridium Difficile* is a main pathogenic bacterium which causes diarrhea in patients due to antibiotic use. The symptoms comprise slight diarrhea and serious intestinal inflammation, such as pseudomembranous enteritis, toxic megacolon, and bacteriemia, which may cause death if the symptoms become serious enough. *Clostridium Difficile* can be spread in spore form. In past studies, it was found that the *Clostridium difficile* infection (*C. difficile* infection; CDI) rate has gradually increasing tendency in Taiwan (Px Zheng, Genome Announc. 2013. 1:e00149-12.). According to statistics by the United States Disease Control Agency, 100,000 American patients die from nosocomial infections and the resulting mortality rate is climbing each year (M F Shih., Int. J. Immunopathol. Pharmacol. 2012. 25:39-48.2). The current clinical treatment of *Clostridium Difficile* is that if the use of antibiotics induces the CDI symptoms, it is recommended to stop the current use of antibiotics, and then use metronidazole and vancomycin in accordance with the severity of the disease. However, the two drugs are ineffective treatments for certain patients or have a high recurrence rate (Y C Lin, 2011. Antimicrob. Agents Chemother. 55: 1701-5.).

In addition to the drug resistance of the *Clostridium Difficile*, a current difficulty of treatment is that the patient cannot generate a proper protective immune response, and this may cause repetitive infection problems. Because the CDI rate in medical care institutions is gradually increasing, and there is a possible recurrence during treatment, the search for non-antibiotic treatment and the improvement for the CDI have become more important problems requiring more attention.

Although it has been found in the past that certain strains of *Lactobacillus* have a strong bacteriostatic ability against *Clostridium Difficile*, which improves the symptoms of mice infected with *Clostridium Difficile*, it has not reported that the lactic acid bacteria can enhance the inflammatory symptoms of CDI through immune-regulation.

It is therefore necessary to provide an anti-inflammatory *Lactobacillus Fermentum* strain and a composition thereof, and a use of the *Lactobacillus Fermentum* strain to produce the composition for improving the symptoms of *Clostridium Difficile* infection, in order to solve the problems existing in the conventional technology as described above.

SUMMARY OF THE INVENTION

A primary object of the present invention is to provide a composition comprising *Lactobacillus Fermentum* GMNL-296 and a use of the *Lactobacillus Fermentum* GMNL-296 to produce the composition for improving symptoms of *Clostridium Difficile* infection so as to stimulate an immune response by the *Lactobacillus Fermentum* GMNL-296, in order to improve weight loss and intestinal abnormalities which the *Clostridium difficile* caused. The *Lactobacillus Fermentum* can be administrated through the esophagus and then enters the digestive system to stimulate the anti-inflammatory cytokine IL-10 (Interleukin-10) secretion and increase the function of the regulatory T cells (Treg), thereby inhibiting and reducing an intestinal inflammation.

To achieve the above objects, the present invention provides a composition for improving symptoms of *Clostridium difficile* infection, comprising *Lactobacillus fermentum* GMNL-296 deposited in the China Center for Type Culture Collection (CCTCC) with an accession number of CCTCC M2016225.

In one embodiment of the present invention, the *Lactobacillus Fermentum* GMNL-296 is a viable strain.

In one embodiment of the present invention, the composition is a pharmaceutical composition, a nutritional supplement, a health food, a medical food, or the combination thereof.

To achieve the above objects, another embodiment according to the present invention provides a use of *Lactobacillus Fermentum* GMNL-296 to produce a composition as described above for improving symptoms of *Clostridium Difficile* infection.

In one embodiment of the present invention, the composition has abilities for stimulating secretion of anti-inflammatory cytokine IL-10, and increasing FoxP3 and GATA3.

In one embodiment of the present invention, the *Lactobacillus Fermentum* GMNL-296 is a viable strain.

In one embodiment of the present invention, the symptoms of *Clostridium Difficile* infection comprise weight loss or intestinal abnormalities.

In one embodiment of the present invention, the intestinal abnormalities comprise a shortened length or thickened diameter of a segment from the colon to the cecum.

DETAILED DESCRIPTION OF THE PREFERRED EMBODIMENTS

Figure 1:
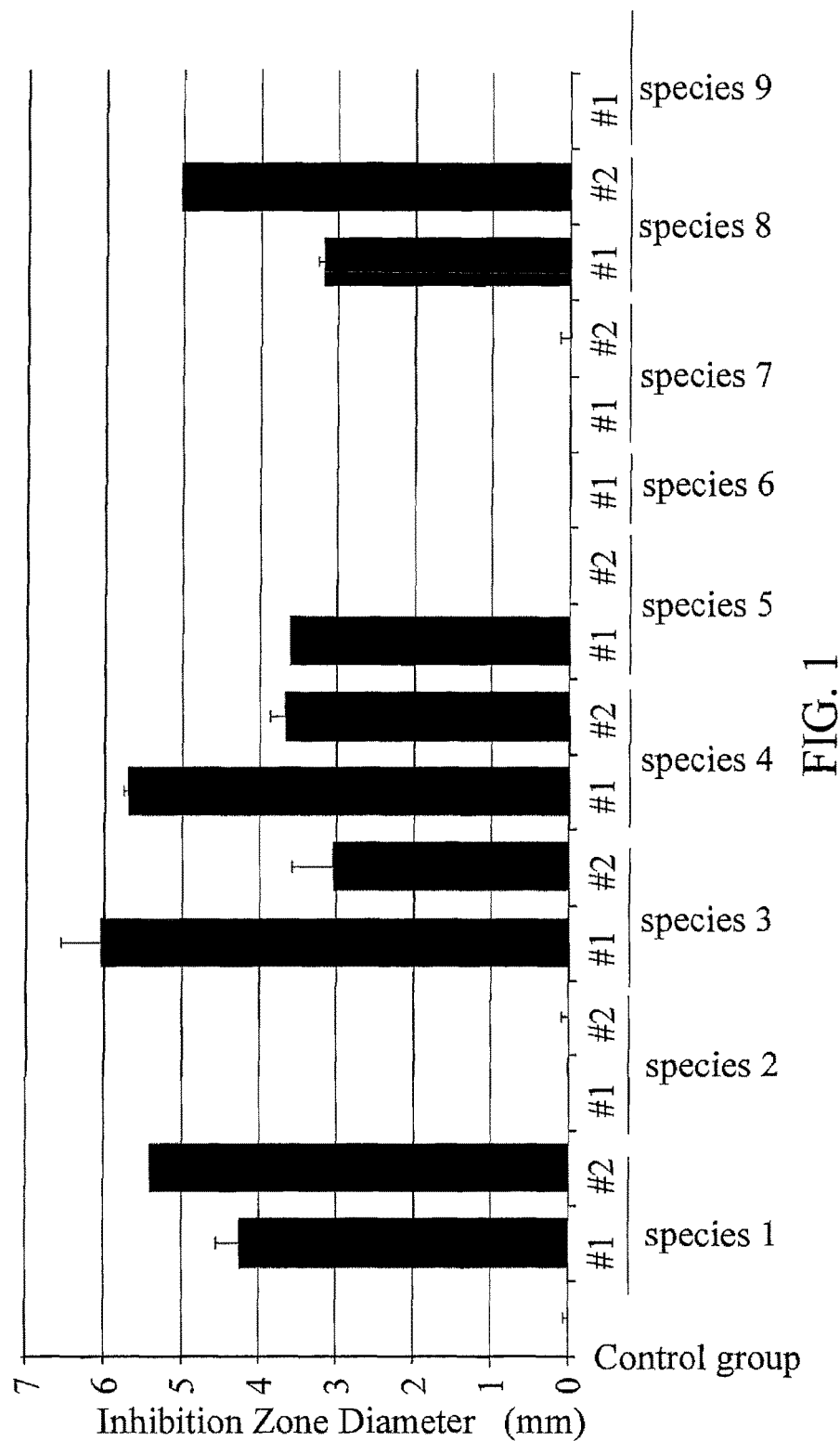
FIG. 1 is a diagram showing the inhibition results of each strain listed in Table 1 to inhibit *Clostridium Difficile* in the experiment 1 according to one embodiment of the present invention.

The structure and the technical means adopted by the present invention to achieve the above and other objects can be best understood by referring to the following detailed description of the preferred embodiments. Furthermore, if there is no specific description in the invention, singular terms such as "a", "one", and "the" include the plural number. For example, "a compound" or "at least one compound" may include a plurality of compounds, and the mixtures thereof. If there is no specific description in the invention, "%" means "weight percentage (wt %)", and the numerical range (e.g. 10%-11% of A) contains the upper and lower limit (i.e. 10%≤A≤11%). If the lower limit is not defined in the range (e.g. less than, or below 0.2% of B), it means that the lower limit may be 0 (i.e. 0%≤B≤0.2%). The proportion of "weight percent" of each component can be replaced by the proportion of "weight portion" thereof. The abovementioned terms are used to describe and understand the present invention, but the present invention is not limited thereto.

One embodiment of the present invention provides a *Lactobacillus fermentum* strain for improving symptoms of *Clostridium difficile* infection. The *Lactobacillus fermentum* strain is referred to as *Lactobacillus fermentum* GMNL-296, which is deposited in the China Center for Type Culture Collection (CCTCC) with an accession number of CCTCC M2016225.

One embodiment of the present invention provides a composition, comprising the abovementioned *Lactobacillus Fermentum* strain, which can improve the symptoms of *Clostridium Difficile* infection. Preferably, the composition can be a pharmaceutical composition, a nutritional supplement, a health food, a medical food, or the combination thereof. The composition can be formed in various form based on the effectivity or convenience. In addition, the composition is preferably administrated by means of food to enter the digestive system, and can stimulate an immune response to inhibit the intestinal inflammation.

One embodiment of the present invention provides a use of *Lactobacillus Fermentum* GMNL-296 to produce a composition for improving infection symptoms of *Clostridium difficile*, comprising the following steps of: using the abovementioned *Lactobacillus Fermentum* GMNL-296 viable strain to promote the mRNA expression of Treg related transcription factors, FoxP3 and GATA3, and anti-inflammatory cytokine IL-10, so that the symptoms, such as weight loss or intestinal abnormalities caused by the *Clostridium Difficile*, can be improved. The intestinal abnormalities means a general inflammation of the rectum, colon to cecum segment, and the appearance thereof show a shortened length or a thickened diameter.

The *Lactobacillus Fermentum* strain GMNL-296 in the abovementioned embodiments is one of a plurality of isolates mainly isolated from human intestines. The primers (SEQ ID NO: 1 and SEQ ID NO: 2) listed in Table 1 are used to perform PCR to reproduce 16S rDNA segments of each isolate, and then sequencing the 16S rDNA segment of each isolate. After sequencing, a 16S rDNA gene sequence of one of the isolates can be obtained as below (SEQ ID NO: 3); subsequently, from the comparison results on the NCBI website, it shows that the 16S rDNA sequences of the isolates are similar to that of the *Lactobacillus Fermentum* strains with identities all over 99%, so that the strain GMNL-296 indeed belongs to the *Lactobacillus Fermentum* genus.

TABLE 1

PCR primer

| Primer | SEQ ID NO: | SEQ |
|---|---|---|
| PAF | 1 | AGA GTT TGA TCC TGG CTC AG |
| 536R | 2 | GTA TTA CCG CGG CTG CTG |

TABLE 2

| NCBI NO | Description | Identity |
|---|---|---|
| NC 021235.1 | *Lactobacillus fermentum* F-6 | 100% |
| NC 017465.1 | *Lactobacillus fermentum* CECT 5716 | 100% |
| NC 010610.1 | *Lactobacillus fermentum* IFO 3956 DNA | 99% |
| NZ CP011536.1 | *Lactobacillus fermentum* 3872 | 99% |

A complete 16S rDNA sequence (SEQ ID NO: 3) of the *Lactobacillus fermentum* strain GMNL-296 is listed as below:

GGGATACATGCAAGTCGAACGCGTTGGCCCAATTGATTGAT

GGTGCTTGCACCTGATTGATTTTGGTCGCCAACGAGTGGCGGACGGGTG

AGTAACACGTAGGTAACCTGCCCAGAAGCGGGGGACAACATTTGGAAAC

AGATGCTAATACCGCATAACAACGTTGTTCGCATGAACAACGCTTAAAAG

ATGGCTTCTCGCTATCACTTCTGGATGGACCTGCGGTGCATTAGCTTGTT

GGTGGGGTAACGGCCTACCAAGGCGATGATGCATAGCCGAGTTGAGAG

ACTGATCGGCCACAATGGGACTGAGACACGGCCCATACTCCTACGGGA

GGCAGCAGTAGGGAATCTTCCACAATGGGCGCAAGCCTGATGGAGCAA

CACCGCGTGAGTGAAGAAGGGTTTCGGCTCGTAAAGCTCTGTTGTTAAA

GAAGAACACGTATGAGAGTAACTGTTCATACGTTGACGGTATTTAACCAG

AAAGTCACGGCTAACTACGTGCCAGCAGCCGGGG

A fermentation test to the *Lactobacillus fermentum* strain GMNL-296 is carried out to obtain the results shown in Table 3

TABLE 3

Fermentation Test

| Strips No. | carbohydrates substrate | GMNL-296 |
|---|---|---|
| 0 | CONTROL | − |
| 1 | Glycerol | − |
| 2 | Erythritol | − |
| 3 | D-Arabinose | − |
| 4 | L-Arabinose | + |
| 5 | D-Ribose | + |
| 6 | D-Xylose | − |
| 7 | L-Xylose | − |
| 8 | D-Adonitol | − |
| 9 | Methyl-β-D-Xylopyranoside | − |
| 10 | D-Galactose | + |
| 11 | D-Glucose | + |
| 12 | D-Fructose | + |
| 13 | D-Mannose | + |
| 14 | L-Sorbose | − |
| 15 | L-Rhamnose | − |
| 16 | Dulcitol | − |
| 17 | Inositol | − |
| 18 | D-Mannitol | − |
| 19 | D-Sorbitol | − |

TABLE 3-continued

Fermentation Test

| Strips No. | carbohydrates substrate | GMNL-296 |
|---|---|---|
| 20 | Methyl-α-D-mannopyranoside | − |
| 21 | Methyl-α-D-glucopyranoside | − |
| 22 | N-Acetyl glucosamine | − |
| 23 | Amygdalin | − |
| 24 | Arbutin | − |
| 25 | Esculin ferric citrate | − |
| 26 | Salicin | − |
| 27 | D-Cellobiose | − |
| 28 | D-Maltose | + |
| 29 | D-Lactose (bovine origin) | + |
| 30 | D-Melibiose | + |
| 31 | D-Saccharose (sucrose) | + |
| 32 | D-Trehalose | + |
| 33 | Inulin | − |
| 34 | D-Melezitose | − |
| 35 | D-Raffinose | + |
| 36 | Amidon (starch) | − |
| 37 | Glycogen | − |
| 38 | Xylitol | − |
| 39 | Gentiobiose | − |
| 40 | D-Turanose | − |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Potassium gluconate | + |
| 48 | Potassium 2-ketogluconate | − |
| 49 | Potassium 5-ketogluconate | − |

−: negative;
+: positive

To verify the anti-inflammatory properties of the *Lactobacillus Fermentum* GMNL-296 according to the present invention, and to confirm that the infection symptoms caused by the *Clostridium Difficile* can be improved, experiments 1 to 3 are executed.

EXPERIMENT 1

Pathogen Treatment:
Incubating the *Clostridium Difficile* pathogens (*Clostridium* VPI10463) overnight, and then scraping and suspending the *Clostridium Difficile* pathogens in 0.5 ml BHIS broth. Next, measuring the concentration of the pathogens in the broth, and adjusting the concentration to $1\times10^{10}$ CFU/ml. Then, incubating the pathogens using 100 µl of broth having the concentration of $1\times10^{10}$ CFU/ml in a pathogen culture plate.

Lactic Acid Bacteria Treatment:
Incubating the *Lactobacillus Fermentum* GMNL-296 overnight with a concentration of $1\times10^8$ CFU/ml and other lactic acid bacteria (as control groups) listed in Table 4, and collecting supernatants containing viable strains from each group, respectively. Filtering with 0.22 µm filter membranes (#1), and the MRS broth is titrated with HCl to have a pH value the same as the original supernatant to serve as control groups (#2). Obtaining 100 µl of sample containing corresponding lactic acid bacteria from each group, and adding the sample to the holes drilled on the pathogen culture plate. Next, placing into an anaerobic incubator and incubating overnight. Subsequently, measuring the inner diameter and the outer diameter of the of the inhibition zone with a caliper.

TABLE 4

| Group | Species name | Strain No. |
|---|---|---|
| 1 | L. rhamnosus | #1、#2 |
| 2 | L. fermentum GMNL-296 | #1、#2 |
| 3 | L. plantarum | #1、#2 |
| 4 | L. paracasei | #1、#2 |
| 5 | L. salivarius | #1、#2 |
| 6 | L. bulgaricus | #1 |
| 7 | L. brevis | #1、#2 |
| 8 | L. pentosus | #1、#2 |
| 9 | L. reuteri | #1 |

The experiment results are shown in FIG. 1. From FIG. 1, it can be seen that the species 2 (#1, i.e. the viable strain solution of *L. fermentum* GMNL-296) has no obvious inhibition to the growth of *Clostridium* VPI10463, and the control group (MRS, pH=4.0) also shows no inhibition zone. Therefore, it can be understood that the *Lactobacillus Fermentum* GMNL-296 cannot directly inhibit the growth of *Clostridium Difficile*.

EXPERIMENT 2

Bacteria Broth Culture:
Inoculating the *Lactobacillus Fermentum* GMNL-296 from a frozen tube to 1 ml of MRS broth, and standing under 37° C. for aerobically incubating for 20 hours. The next day, adding 15 µl culture solution into 1.5 ml of MRS broth (1% secondary activation), and then standing under 37° C. for aerobically incubating for 20 hours.

Cell Culture:
Adjusting the cell number of macrophage cells (RAW 264.7) to $8\times10^5$ cells/ml. Adding 0.5 ml of cell solution (with a final cell number of $4\times10^5$ cells/well) into a 24-well plate, and standing at 37° C. overnight. Next, using phosphate buffer saline (called PBS hereinafter) to clean the 24-well plate one time, and then replacing the culture medium with 0.4 ml/well culture medium without serum (DMEM) to execute starvation for 2 hours.

Co-Culture of Bacteria and Cell:
Taking the bacteria solution, which was incubated the previous night, to centrifugate for 1 minute (13000 rpm), and carrying out PBS washing twice. After removing the supernatant again, having 20 µl of PBS suspension of bacteria to mix with 980 µl of PBS (dilute 50 fold). Measuring OD 600, estimating back to adjust the bacteria concentration to $1\times10^{10}$ CFU/ml. Having 0.2 ml of the adjusted bacterial solution to mix with 0.8 ml of DMEM (without serum), so that the final number of the bacteria comes to $2\times10^9$ CFU/ml. The final concentration was previously adjusted in the sequence of $2\times10^9$, $1\times10^9$, $5\times10^8$, $1\times10^8$, $5\times10^7$ CFU/ml. After cell starvation is executed for 2 hours, adding 100 µl of the bacteria solutions having different diluting folds for treating the cells for 2 hours.

Continuously adding 0.5 ml DMEM, including 200 ng/ml of LPS, into each hole after the co-culture of the bacteria solution and the cells are executed for 2 hours; and the control group (mock) is provided by adding 0.5 ml DMEM. Culturing together again for 20 hours, collecting the supernatant for measuring NO (nitric oxide) content of each group.

Figure 2:
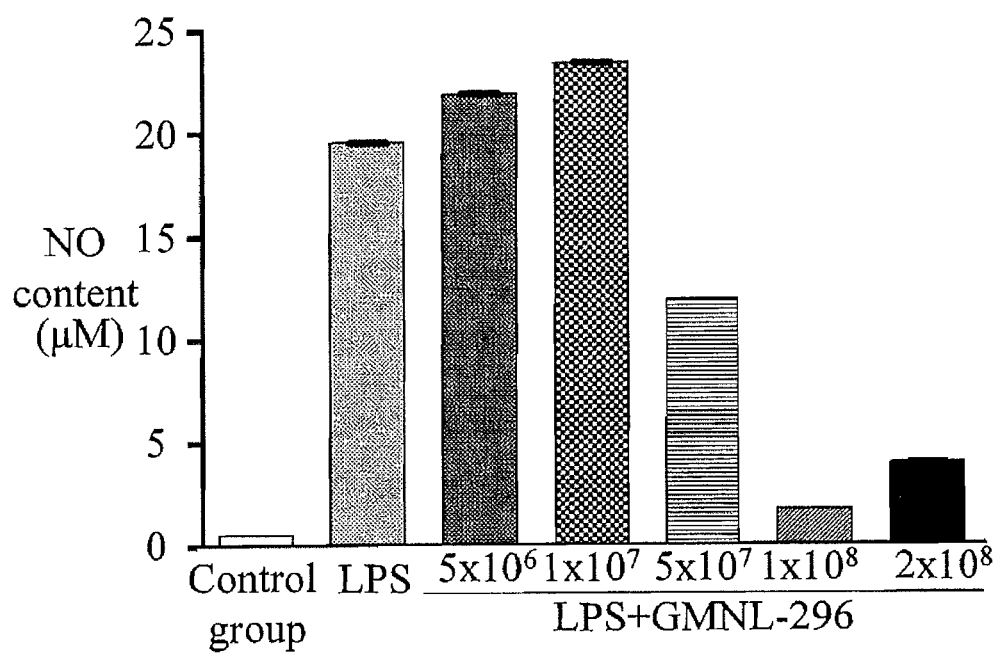
FIG. 2 shows the effect of different doses of *Lactobacillus Fermentum* strain GMNL-296 on NO content in the anti-inflammatory test of the experiment 2.

Mixing NO reagent (80 µl Griess reagent A+80 µl Griess reagent B) with 80 µl cell supernatant to react together under room temperature for 5 minutes. Next, using an ELISA reader to determine absorbance value of OD 550 nm. The results are shown in FIG. 2. It can be found that LPS can effectively promote the generation of NO which is the inflammatory substance of RAW264.7 cells. In addition, after pre-treating with different doses of GMNL-296, with the increase of the dose of GMNL-296, the content of NO is gradually reduced, especially for the doses from $5 \times 10^7$ CFU/ml to $2 \times 10^8$ CFU/ml, there is found a significant decline compared to the group without GMNL-296 but only with LPS, and which means that the *Lactobacillus Fermentum* GMNL-296 is capable of inhibiting the inflammation within a specific range of doses, and is a strain having anti-inflammatory ability. Therefore, the *Lactobacillus Fermenturn* GMNL-296 can effectively inhibit the inflammation generated by stimulating RAW264.7 cells by LPS.

EXPERIMENT 3

Experiment Material: 7-8 weeks-old mice (C57BL/6) and *Lactobacillus Fermentum* GMNL-296 live bacteria powder.
Experiment Process:
Pipe-feeding the 7-8 weeks-old mice (C57BL/6) every day with GMNL-296 bacteria solution ($4*10^8$ CFU/kg). Continuously feeding for 10 days, performing disease animal model at the fifth day, and administrating 0.4 mg/ml of kanamycin, 0.057 mg/ml of gentamycin, 0.057 mg/ml of colistin, 0.215 mg/ml of metronidazole, 0.045 mg/ml of vancomycin for 5 days. Moreover, pipe-feeding 40 mg/kg/day of proton pump inhibitor (PPI), Esomeprazole (Nexium), per 12 hours starting from the fourth day of administrating the antibiotics. In addition, the bacteria solution of GMNL-296 is replaced with PBS as being the control group to performing the abovementioned process.

On the fifth day, removing metronidazole and vancomycin. On the day of infection, 4 mg/kg of clindamycin is administrated by intraperitoneal injection, and each mice is fed with *Clostridium Difficile* (*Clostridium* VPI10463) in an amount of $1 \times 10^8$ cfu. During this process, keeping pipe-feeding the mice with the GMNL-296.

The changes of body weight are observed and the length of the intestines is dissected. The Treg-related transcription factors FoxP3 and GATA3 and the mRNAs that can inhibit the expression of inflammatory cytokines IL-10 are analyzed by real-time PCR and the RNA is extracted from the mouse intestinal tissue and purified.

Figure 3A:
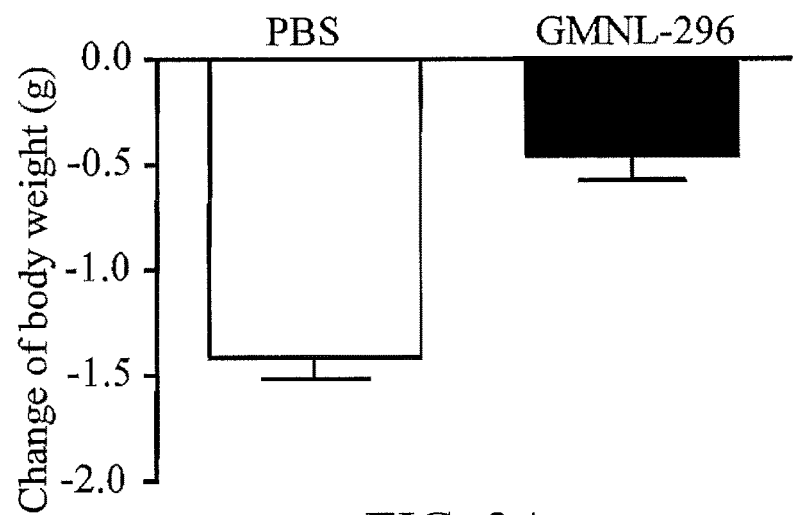
FIGS. 3A and 3B show the effects on *Clostridium Difficile*-infected mice after feeding *Lactobacillus Fermentum* strain GMNL-296 or phosphate saline (PBS) in the experiment 3.
Figure 3B:
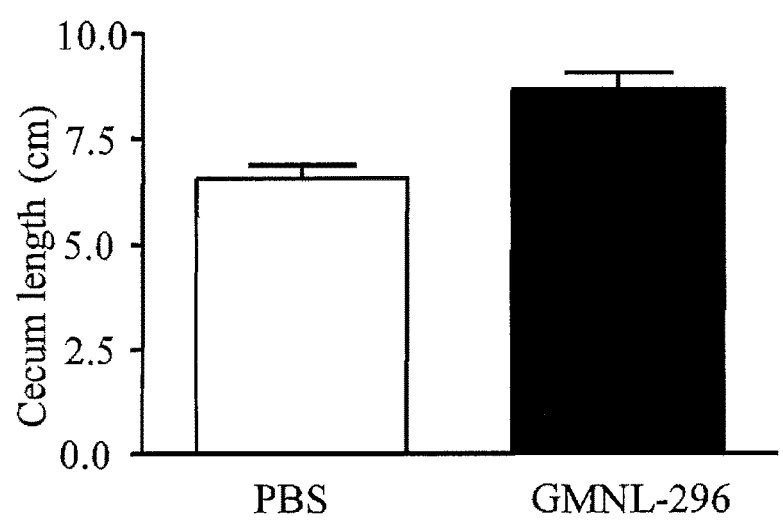

From Experiment 3, it can be found that the mice infected with *Clostridium Difficile* will indeed cause intestinal inflammatory, including weight loss and shortened length of cecum to colon segment. Referring to FIGS. 3A and 3B, the group fed with GMNL-296 is effective in protecting the mice from the symptoms of weight loss (FIG. 3A) and shortened length of the cecum to colon segment (FIG. 3B) caused by *Clostridium Difficile* infection. From the above results, it can be shown that *Lactobacillus Fermentum* GMNL-296 can improve cecum and colon segment abnormalities caused by *Clostridium Difficile* infection.

Figure 4:
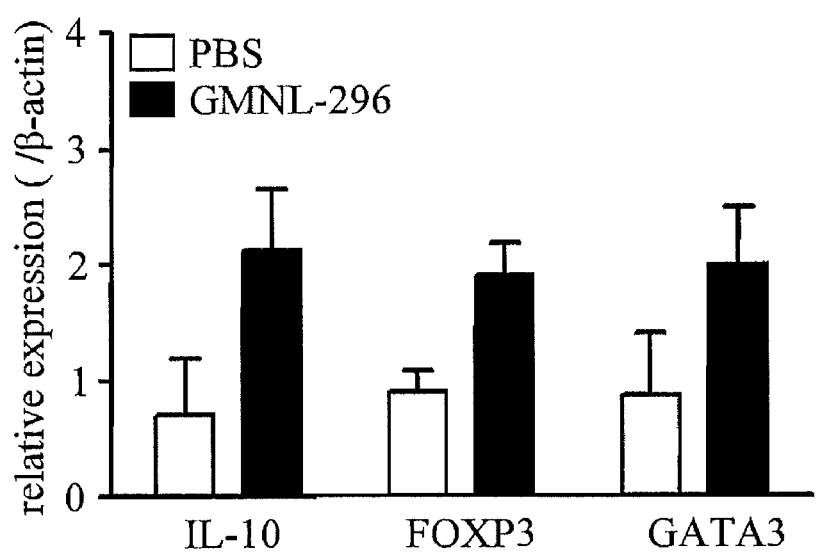
FIG. 4 shows mRNA expression of anti-inflammatory cytokine IL-10 and Treg cell related transcription factors, FoxP3 and GATA3, of *Clostridium Difficile*-infected mice after feeding *Lactobacillus Fermentum* strain GMNL-296 or phosphate saline (PBS) in the experiment 3.

Furthermore, refer to FIG. 4, which shows mRNA expression of transcription factors FoxP3 and GATA3 and anti-inflammatory cytokine IL-10. It can also be found from FIG. 4 that the administration of *Lactobacillus Fermentum* GMNL-296 can promote FoxP3 genes in the mice intestinal tissue; and promote the secretion of anti-inflammatory cytokine IL-10. These two molecules are most related to the activation of Treg. GMNL-296 can activate the generation of regulatory T cells through increasing these molecules to achieve immune regulation. In addition, it is also found that GMNL-296 has the ability to increase the expression of GATA3 (Trans-acting T-cell-specific transcription factor 3) gene which is an important transcription factor associated with the regulatory T cells, through this molecule, GMNL-296 can improve the immune disorders caused by acute infection of *Clostridium Difficile*. From this result, the *Lactobacillus Fermentum* GMNL-296 can improve intestinal abnormalities caused by *Clostridium Difficile* infection mainly by increasing the expression of FoxP3, IL-10, and GATA3 gene in the intestine tissue to regulate the immune response, rather than by inhibiting the growth of *Clostridium difficile*.

In summary, it can be confirmed that the *Lactobacillus Fermentum* GMNL-296 and the use thereof to produce a composition for improving *Clostridium Difficile* infection are successful constructions in an animal model. The infected mice have disease characterizations close to that of humans, such as severe diarrhea, weight loss, ulcers of cecum and large intestine, or even death. From the experiment results, it can be found that the *Lactobacillus Fermentum* (GMNL-296) indeed has improvements of the weight loss and shortened intestine length caused by *Clostridium Difficile*. That is, the *Lactobacillus Fermentum* GMNL-296 can prevent and treat malignant symptoms due to *Clostridium difficile* infection. In addition, through promoting the expression of the Treg related molecules FoxP3 and IL-10, as well as a few increase of GATA3, the *Lactobacillus Fermentum* GMNL-296 improves the symptoms of *Clostridium Difficile* infection that is significantly different from the direct inhibition to the growth of *Clostridium Difficile*. Thus, the improvement mechanism of *Clostridium Difficile* infection is obviously different from the past.

The present invention has been described with preferred embodiments thereof and it is understood that many changes and modifications to the described embodiments can be carried out without departing from the scope and the spirit of the invention that is intended to be limited only by the appended claims.

What is claimed is:

1. A method of treating *Clostridium difficile* infection, comprising a step of:

administrating to a subject in need thereof an effective amount of a composition comprising *Lactobacillus* fermentum GMNL-296 and a pharmaceutically acceptable carrier, wherein the *Lactobacillus* fermentum GMNL-96 is deposited in the China Center for Type Culture Collection (CCTCC) with an accession number of CCTCC M2016225 on 25 Apr. 2016.

2. The method according to claim 1, wherein the *Lactobacillus* fermentum GMNL-296 is a viable strain.

3. The method according to claim 1, wherein the composition is a phaitnaceutical composition, a nutritional supplement, a health food, a medical food, or combination thereof.

4. The method according to claim 1, wherein the composition stimulates secretion of anti-inflammatory cytokine IL-10, and increasing FoxP3 and GATA3.

5. The method according to claim 1, wherein symptoms of *Clostridium difficile* infection comprise weight loss or intestinal abnormalities.

6. The method according to claim 5, wherein the intestinal abnormalities comprise a shortened length or thickened diameter of a segment from the colon to the cecum.

* * * * *